United States Patent [19]

Asnis et al.

[11] 4,450,835
[45] May 29, 1984

[54] METHOD AND SYSTEM FOR INSERTING A SURGICAL WIRE

[75] Inventors: Stanley E. Asnis, Port Washington, N.Y.; Rocco R. Borzone, Emerson, N.J.

[73] Assignee: Howmedica, Inc., New York, N.Y.

[21] Appl. No.: 468,245

[22] Filed: Feb. 22, 1983

Related U.S. Application Data

[62] Division of Ser. No. 236,089, Feb. 20, 1981, Pat. No. 4,383,527.

[51] Int. Cl.³ .............................................. A61F 5/04
[52] U.S. Cl. ......................... 128/92 EB; 128/92 BA; 128/92 BB
[58] Field of Search .............. 128/92 A, 92 B, 92 BA, 128/92 BB, 92 R, 92 EB; 408/241 B, 241 G

[56] References Cited

U.S. PATENT DOCUMENTS

| | | | |
|---|---|---|---|
| 2,200,120 | 5/1940 | North | 128/83 |
| 2,301,500 | 11/1942 | Anderson | 128/83 |
| 2,531,734 | 11/1950 | Hopkins | 128/83 |
| 2,607,339 | 8/1952 | Price | 128/92 |
| 2,625,934 | 1/1953 | Halliday | 128/303 |
| 2,697,433 | 12/1954 | Zehnder | 128/83 |
| 2,937,642 | 5/1960 | Lange et al. | 128/92 |
| 3,135,263 | 6/1964 | Connelley | 128/303 |
| 3,587,560 | 6/1971 | Glassman | 128/753 |
| 3,704,707 | 12/1972 | Halloran | 128/92 EB |
| 3,892,232 | 7/1975 | Neufeld | 128/92 EB |
| 3,945,377 | 3/1976 | Kronner | 128/92 EB |
| 4,037,592 | 7/1977 | Kronner | 128/92 EB |
| 4,050,528 | 9/1977 | Foltz et al. | 173/163 |
| 4,157,714 | 6/1979 | Foltz et al. | 128/92 B |
| 4,306,570 | 12/1981 | Matthews | 128/754 |
| 4,383,527 | 5/1983 | Asnis et al. | 128/92 EB |

FOREIGN PATENT DOCUMENTS

| | | | |
|---|---|---|---|
| 910078 | 5/1946 | France | 128/92 EB |
| 910763 | 6/1946 | France | 128/92 EB |
| 227453 | 9/1943 | Switzerland | 128/92 EB |
| 579985 | 11/1977 | U.S.S.R. | 128/92 EB |

OTHER PUBLICATIONS

Engel, Gilson C. et al. "Two-Plane Direction Finder for Nailing Fractures of Neck of Femur", Surg., Gyn. & Obstetr., pp. 495-499, Feb. 1938.

Durnin, W.G., "An Angled Guide-Wire Director for Use in Treatment of Intertrochanteric Fractures and Fractures of the Neck of the Femur," Jour. Bone and Joint Surg., Vol. 39-A, No. 5, pp. 1203-1205 (Oct. 1957).

"Mecron Cannulated Cancellous Screws," advertisement in Jour. Bone and Joint Surg., October 1979.

Lloyd, E. I. et al., "A Director for the Insertion of the Smith-Petersen Nail", The Lancet, pp. 129-131 (July 20, 1935).

"The Howse Cannulated Screw," D. Howse and Co., Ltd. catalog, pp. 30-31.

Primary Examiner—C. Fred Rosenbaum
Assistant Examiner—C. W. Shedd
Attorney, Agent, or Firm—Lawrence C. Akers; Peter C. Richardson; Charles J. Knuth

[57] ABSTRACT

A novel method and system for inserting a surgical wire into a patient's bone is disclosed. The novel system includes a novel tool for guiding a surgical wire into the patient's bone at a universally adjustable position in relation to a previously inserted wire, and a novel guide pin-external sleeve combination whose use greatly facilitates the steps of guide pin insertion and, after the sleeve has been removed, insertion of a cannulated surgical implant over the guide pin. The novel system is particularly suited for use in a surgical procedure for fixing a fracture in the femoral neck with a plurality of parallel cannulated bone screws.

5 Claims, 15 Drawing Figures

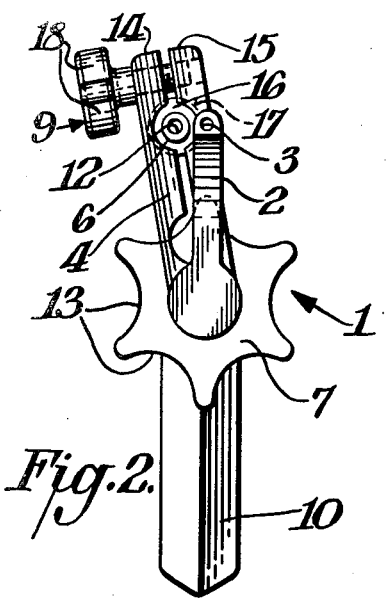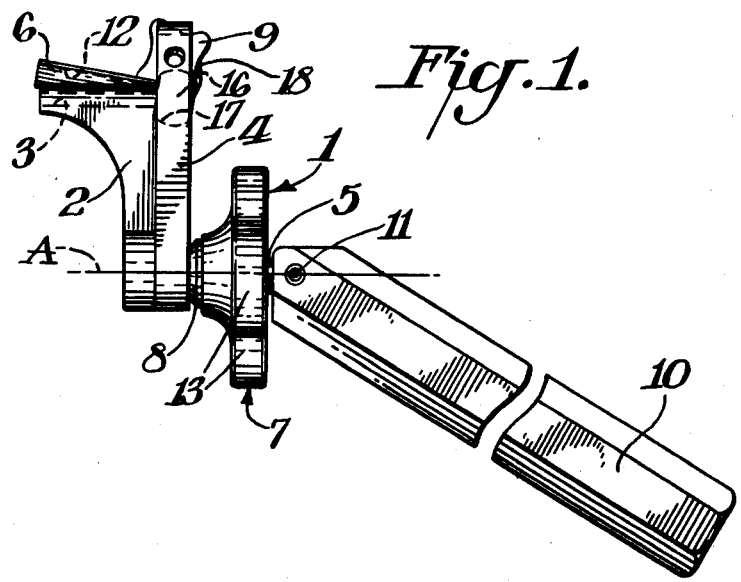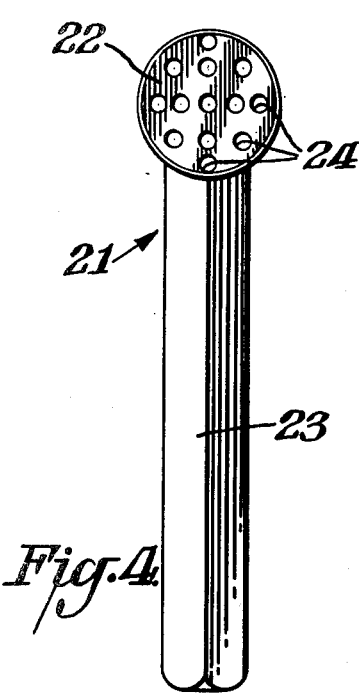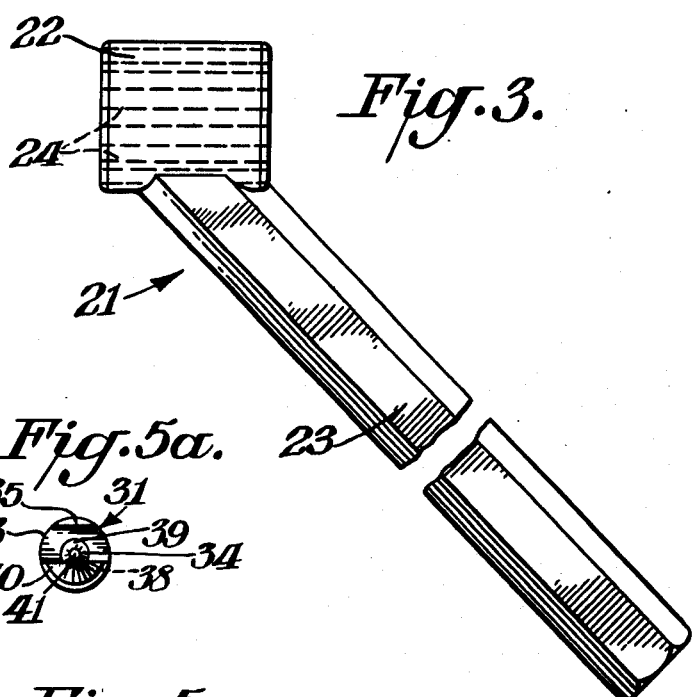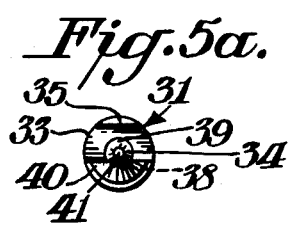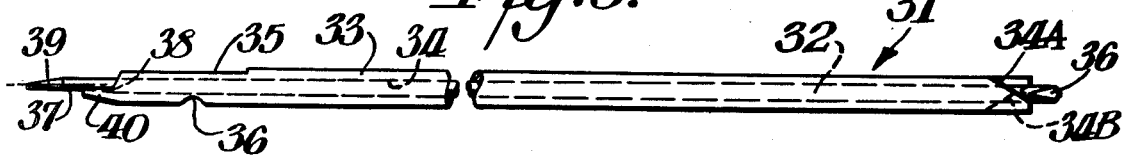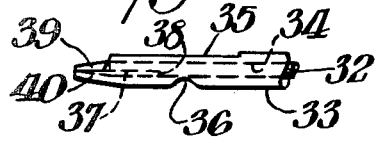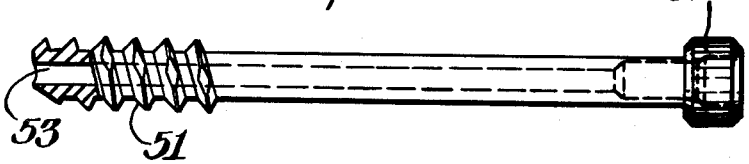

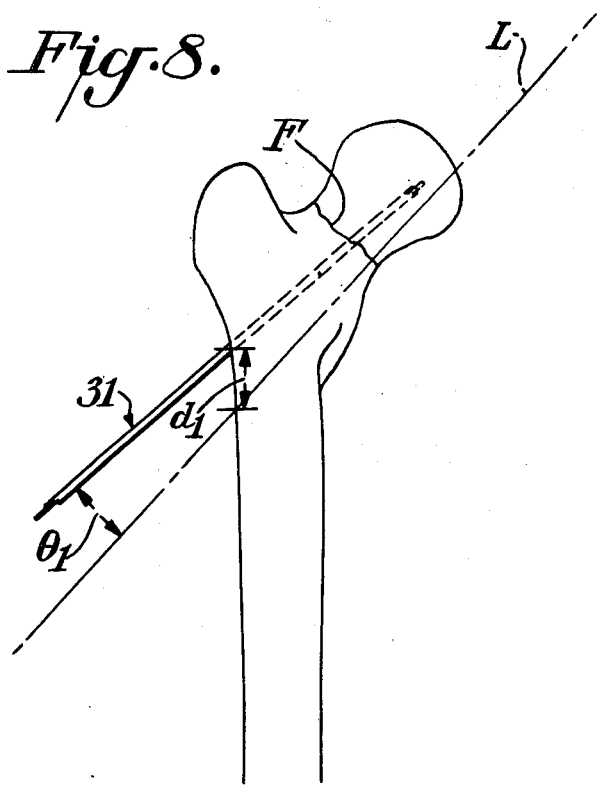
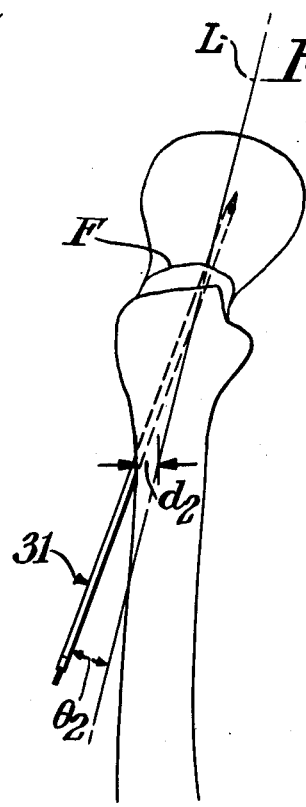
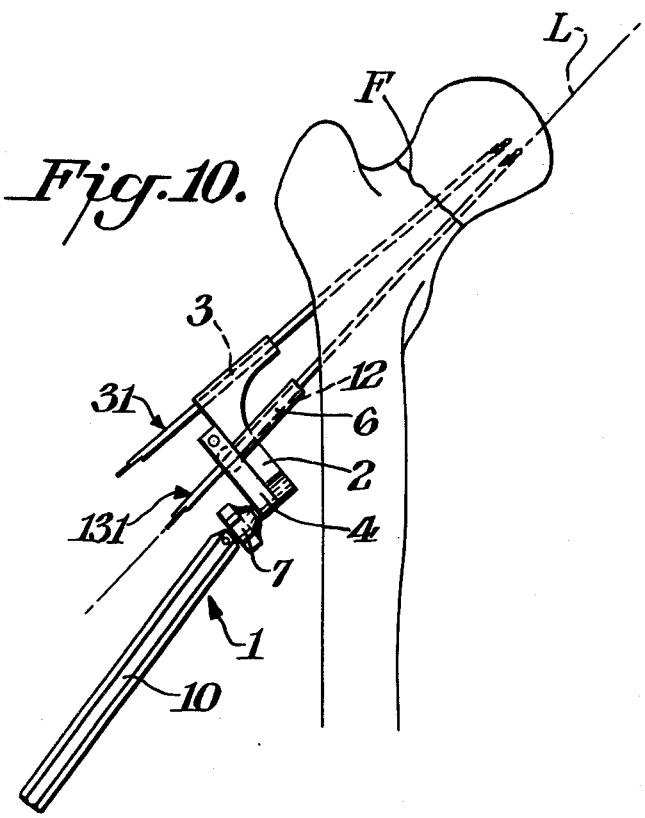

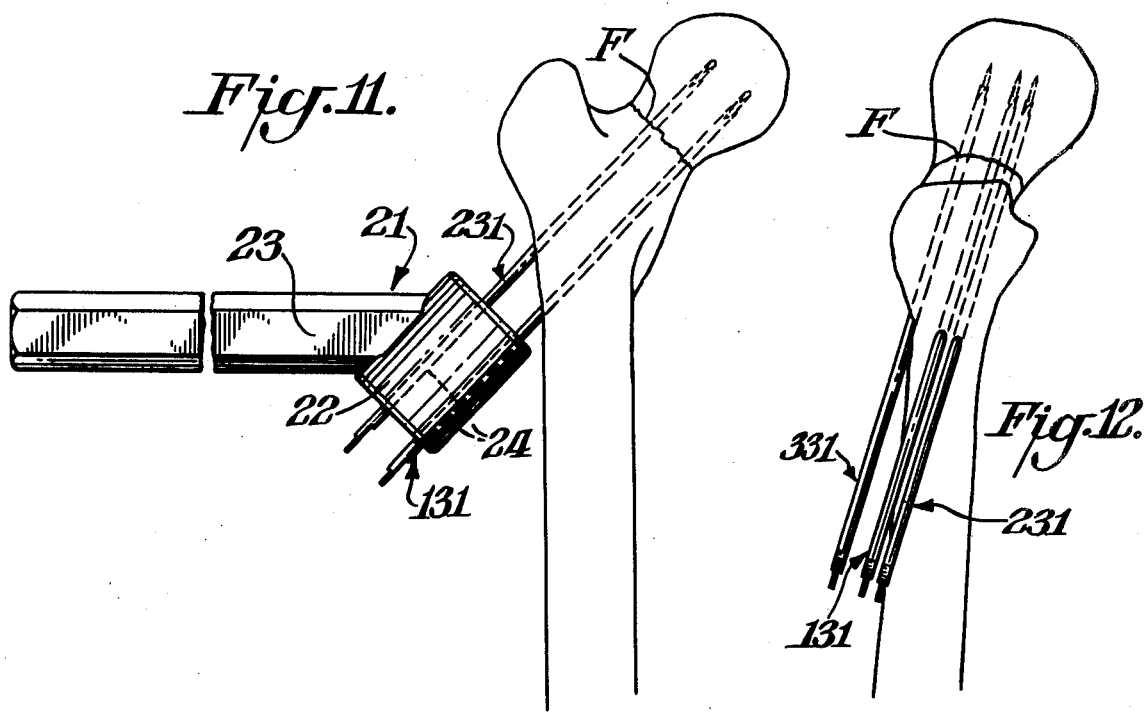
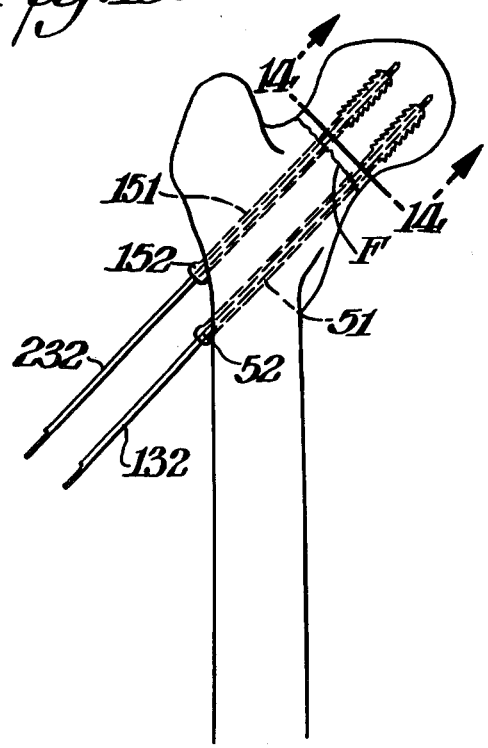
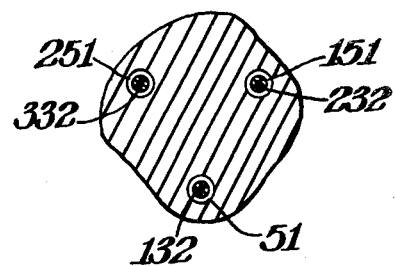

METHOD AND SYSTEM FOR INSERTING A SURGICAL WIRE

This is a division of application Ser. No. 236,089, filed on Feb. 20, 1981 now U.S. Pat. No. 4,383,527

BACKGROUND OF THE INVENTION

A variety of techniques are known in the surgical arts in which a plurality of surgical implants, e.g. bone prostheses, are inserted into the bone of a patient. Commonly, the goal of such a technique is the stabilization and subsequent healing of a fracture across which a plurality of bone prostheses, e.g. screws, nails or pins, are placed, preferably in a mutually parallel relationship. In one technique in common use, especially in the fixation of fractures of the femoral neck, non-cannulated Knowles pins threaded at their proximal ends are drilled by the surgeon into position across the fracture. This is essentially a "free-hand" procedure aided by X-rays taken in the anterior-posterior and lateral planes before and after pin placement; thus correct placement requires the exercise of a considerable amount of technical skill. Incorrectly positioned pins must be removed, thereby leaving an undesired bore in the patient's bone, and re-drilled into the correct position. The use of jigs to insure the proper placement of Knowles pins is complicated by the fact that these pins are headed at their distal ends to provide means for applying compression to the fragments of the fractured bone. Replacement of a correctly positioned Knowles pin with one of a different length may also be problematic in cancellous bone because of the difficulty in following the existing bore in the spongy bone tissue.

Certain of the difficulties mentioned above can be alleviated by the use of cannulated bone screws inserted over previously inserted guide wires (see for example U.S. Pat. No. 2,570,465), with the cannulation being as narrow as possible to provide the necessary screw strength with a minimum screw outer diameter. Most commonly, the guide wires are drilled into position by the same "free-hand" method described above in connection with Knowles pinning. The consquent difficulties in properly positioning the guide wires are compounded by the tendency of the narrow wires to wobble and bend as they are drilled into position.

A number of instruments intended for positively directing the correct placement into bone of prostheses or guide wires therefor have been disclosed in the prior art. As a rule, these instruments suffer in use from one or more of the following drawbacks: (a) they are complex in design and cumbersome and time-consuming to operate; (b) they require unnecessary destruction of healthy tissue (e.g., lengthy incisions, fixations of instruments to bone with screws) during the surgical intervention; or (c) they do not provide for universal positioning (in terms of both linear displacement and angulation) of the prosthesis or guide wire in the patient's bone.

SUMMARY OF THE INVENTION

It is an object of the present invention to provide a method and system for accurately and conveniently inserting a surgical wire into a predetermined position in the bone of a patient, which method and system substantially alleviate the disadvantages described above. This and other objects of the invention are achieved with the use of an improved surgical system including, as important components thereof, a novel adjustable tool for use in inserting a second surgical wire into the bone of a patient at a different (correct) position from that of a first (incorrectly positioned) surgical wire previously inserted therein, and a novel surgical guide pin - external sleeve combination.

The novel adjustable tool of the invention comprises a first arm adapted to receive and rotate about the axis of the first wire, a second arm rotatable with respect to said first arm about an axis of rotation parallel to the first wire, and means connected to the second arm for receiving and directing the placement of the second wire, with the connection of said receiving and directing means to the second arm being such that the second wire can be universally angulated with respect to the second arm about a center of rotation, and with the distance between said center of rotation and said axis of rotation being about the same as the distance between said first wire and said axis of rotation. As a result of the synergistic interaction of the several parts of this novel tool, the second surgical wire can be placed at virtually any position in the bone of the patient not occupied by the first wire, i.e. both linear displacement and angulation of the second wire relative to the first wire can be adjusted essentially universally in the patient's bone. This adjustable tool is adapted to be used in a surgical procedure in which the first surgical wire is inserted "free-hand-38 into the patient's bone. If X-rays reveal that this first wire has been incorrectly positioned, the adjustable novel tool is used, as will be explained herein, to direct the second wire into the correct position. In stating herein that the second wire can be universally angulated with respect to the first wire or the second arm, it is meant that universal angulation is achievable in a practical sense, i.e., within the broad limits established by the anatomical dimensions relevant to the intented use (e.g., fixation of a fracture of the femoral neck). Thus, for example, it is not necessary to be able to position the second wire so that it is perpendicular to the first wire. Likewise, it is not necessary to be able to position the second wire at a linear displacement from the first wire greater than twice the distance between the first wire and the axis of rotation between the first and second arms.

Preferably, the novel adjustable tool contains first releasable means for locking the rotational position of he first arm with respect to the second arm and second releasable means for locking the angular position of the receiving and directing means for the second wire, preferably a guide tube, with respect to the second arm. It is also preferred that the novel tool contain a handle integral with said first arm and adapted to be held in the hand of the user, thereby facilitating the application and manipulation of the tool. Furthermore, it is preferred that the connection of the receiving and directing means for the second wire, e.g. a guide tube, to the second arm of the tool be that of a ball-and-socket joint.

The novel guide pin - external sleeve combination of the invention comprises a surgical guide pin having a distal end, a proximal end and a uniform circular cross-section along the major portion of its length between said two ends and a substantially cylindrical external sleeve having a distal end and a proximal end and receiving the guide pin for sliding fit in a centrally disposed longitudinal bore therein, with the guide pin being longer than the external sleeve, the guide pin and the external sleeve being provided at their proximal ends with cooperating cutting surfaces, and the guide pin and the external sleeve being provided at their distal ends with means interacting to (1) prevent relative rotational movement between the guide pin and the external sleeve when they are in a first relative position in which the distal tip of the guide pin extends beyond the distal tip of the external sleeve and the proximal tip of the guide pin extends beyond the proximal tip of the external sleeve, and (2) permit relative rotational movement between the guide pin and the external sleeve when they are in a second relative position in which the guide pin is displaced proximally relative to said first relative position. Use of this novel combination greatly facilitates the steps of guide pin insertion and subsequent insertion of a cannulated surgical implant over the guide pin. A preferred embodiment of the novel guide pin-external sleeve combination is disclosed below.

The scope of the present invention includes additionally a novel method of inserting a surgical guide pin into the bone of a patient which comprises the steps of inserting said novel combination of the invention into the bone of the patient while the guide pin and the external sleeve are in said first relative position, adjusting said combination so that the guide pin and the external sleeve are placed into said second relative position, and then removing the external sleeve from the bone of the patient while leaving the guide pin in place therein. Preferably, the combination is inserted into the patient's bone with a conventional surgical drill, which may drive either the guide pin or, more preferably, the external sleeve.

As broadly construed, the invention herein includes a method of inserting a guide pin into the bone of a patient wherein a surgical guide pin - substantially cylindrical external sleeve assembly is inserted into the bone of the patient and the external sleeve only is then removed. It inserted with a surgical drill driving both the pin and sleeve, the interacting means discussed above may be omitted.

As used herein the term surgical wire means any straight, substantially cylindrical, non-malleable and non-headed surgical wire or surgical pin. Thus, the term surgical wire includes surgical guide pins. In particular, the term surgical wire includes the novel surgical guide pin-external sleeve combination of this invention. Also as used herein, unless the context clearly dictates otherwise, the term position refers to the location of an object in space in terms of both linear displacement (i.e. translation) and angulation.

The novel adjustable tool and guide pin-sleeve combination are adapted and preferably intended to be used together, particularly in a surgical procedure for the fixation of a fracture in the femoral neck with a plurality of parallel cannulated bone screws. However, it is contemplated that these two instruments may be used independently. Thus, the adjustable tool may be used in the insertion of surgical wires other than the novel combination of the invention, which can be, e.g., conventional guide pins or guide wires (without external sleeves) for cannulated bone prostheses or the ultimate prostheses themselves (e.g. Kirschner wires). Also, the guide pin-external sleeve combination may be used generally in any surgical procedure involving insertion of a guide pin for a cannulated surgical implant. Both the novel adjustable tool and the novel guide pin-external sleeve combination are adapted to be used percutaneously as well as subcutaneously.

DETAILED DESCRIPTION OF THE INVENTION

The invention will be described in detail with reference to a preferred embodiment thereof, which is illustrated in use in a surgical procedure for fixing a fracture in the neck of a right femur with a plurality of cannulated bone screws. Reference to this embodiment and use does not limit the scope of the invention, which is limited only by the scope of the claims. In the drawings:

FIG. 1 is a side view of an adjustable tool of the invention for use in inserting a second surgical wire into the bone of a patient at a different position from that of a first surgical wire previously inserted therein;

FIG. 2 is a front view of the adjustable tool of FIG. 1;

FIG. 3 is a side view of a template tool for use in guiding parallel surgical wires into the bone of a patient;

FIG. 4 is a front view of the template tool of FIG. 3;

FIG. 5 is a side view of a surgical guide pin-external sleeve combination of the invention, with the guide pin and sleeve shown in a first relative position;

FIG. 5a is an enlarged end view (looking in the proximal direction) of the combination of FIG. 5;

FIG. 6 is a side view of the distal ends of the guide pin and sleeve of the combination of FIG. 5, with said guide pin and sleeve shown in a second relative position;

FIG. 7 is a side view, partly in section, of a cannulated bone screw; and

FIGS. 8 to 14 show various steps in a surgical procedure for the fixation of a fracture in the neck of a right femur utilizing the instrumentation illustrated in FIGS. 1 to 7.

A preferred embodiment of the novel adjustable tool of the invention is shown in FIGS. 1 and 2. Adjustable tool 1 comprises a first arm 2 adapted to receive a first surgical wire within cylindrical bore 3 therein, a second arm 4 which slidingly receives rod 5 (which is integral with arm 2) through an aperture (not shown) at one end of arm 4, guide tube 6 with cylindrical bore 12 for receiving and directing the placement of the second surgical wire, locking nut 7 threaded upon rod 5, washer 8, threaded locking screw 9 and handle 10, which is secured to rod 5 by means of set screw 11 and adapted to be held in the hand of the surgeon. Since bore 3 will have the same cross-section as the first surgical wire, arm 2 is free to rotate about the longitudinal axis of said wire. When locking nut 7 is not activated, arm 4 is free to rotate with respect to arm 2 about longitudinal axis A of rod 5. The relative rotational position of arm 4 with respect to arm 2 can be fixed by turning locking nut 7 so as to advance it upon rod 5 and create a friction lock between arms 2 and 4. This friction lock can be released by turning nut 7 in the opposite direction. Locking nut 7 is provided with a plurality of indentations, e.g. 13, so that the surgeon can turn it easily with his fingers. Washer 8 is made of an autoclavable material having appropriate frictional characteristics, such as a linen phenolic material.

As shown in FIG. 2, the main body of arm 4 (except for the portion proximate to rod 5) is split into two branches 14 and 15. The connection of guide tube 6 to arm 4 is that of a ball-and-socket joint comprised of a ball 16 integral with tube 6 and a complimentary socket 17 defined by portions of the inner surfaces of branches 14 and 15. When locking screw 9 is not activated, ball 16 is free to rotate universally within socket 17. The relative angular position of guide tube 6 with respect to arm 4 can be fixed by tightening locking screw 9, thereby clamping ball 16 in a friction lock between branches 14 and 15 of arm 4. This friction lock can be released by turning screw 9 in the opposite direction. The head of screw 9 is provided with a plurality of indentations, e.g. 18, to facilitate turning it with the fingers. As can be seen in FIG. 1, the center of the ball (16)-and-socket (17) joint and the longitudinal axis of bore 3 are equidistant from axis A.

As is best seen in FIG. 2, the combination of the rotation of arm 2 about the first surgical wire in bore 3 with the rotation of arm 4 relative to arm 2 about axis A provides for essentially universal linear displacement in the patient's bone of the second surgical wire in bore 12 with respect to the first surgical wire. In other words, the second wire can be made to enter the bone at virtually any point in the two-dimensional exterior surface of the bone (which will be approximately parallel to the plane of FIG. 2). The third dimension of linear displacement, depth of penetration into the bone, can be easily controlled by the surgeon, e.g. by using a depth gauge or calibrated markings on the second wire. Also, the angulation of ball 16 in socket 17 provides for essentially universal angulation in the patient's bone of the second surgical wire with respect to the first surgical wire.

A template tool 21 for use in guiding a surgical wire into the bone of a patient in a parallel relationship to a surgical wire already inserted therein is shown in FIGS. 3 and 4. Tool 21 comprises a cylindrical head portion 22 integral with a handle 23, adapted to be held in the hand of the surgeon. A plurality of parallel cylindrical bores, e.g. 24, are provided in head 22, as is best shown in FIG. 4.

A preferred embodiment of the novel surgical guide pin - external sleeve combination of the invention is shown in FIGS. 5, 5a and 6. Combination 31 comprises a surgical guide pin 32 having a distal end (at the left in FIG. 5), a proximal end (at the right in FIG. 5) and a uniform circular cross-section along the major portion of its length between said two ends, and a substantially cylindrical external sleeve 33 having a distal end and a proximal end and receiving guide pin 32 for sliding fit in centrally disposed longitudinal bore 34. As can be seen in FIG. 5, guide pin 32 is longer than external sleeve 33, and pin 32 and sleeve 33 are provided at their proximal ends with cooperating cutting surfaces, including surfaces 34A, 34B and 36 and a fourth surface on pin 32 (not shown) identical to surface 36 but facing away from the viewer of FIG. 5, so that the combination can function like a drill bit when the pin and sleeve are in the first relative position shown in FIG. 5. Also, external sleeve 33 is provided with a flat 35 and a part-spherical depression 36 at its distal end to allow the combination to be held in a surgical drill by means of a Trinkle fitting. It is of course possible to provide more than two cutting teeth at the proximal end of sleeve 33, or to provide a different type of cutting shape, e.g. a trocar tip, at the proximal end of pin 32.

Of principal interest are interacting means provided at the distal ends of the guide pin and external sleeve comprising flat 37 on pin 32 extending from the distal tip of the pin to shoulder 38 defining the other end of flat 37, taper 39 on pin 32 extending to the distal tip of the pin with decreasing cross-sectional area and tab 40 extending to the distal tip of sleeve 33 in an inward/distal direction. As can be seen in FIGS. 5 and 6, the length of tab 40 is less than that of flat 37 and about the same as that of taper 39.

When the pin 32 and sleeve 33 are in the first relative position shown in FIG. 5, relative rotational movement between the pin and sleeve are prevented by the impingement of tab 40 against the two longitudinally-extending edges of flat 37 (see FIG. 5a). In the second relative position shown in FIG. 6, the distal tips of the pin and sleeve are flush. Relative rotational movement between the pin and sleeve is now permitted as a result of the clearance between taper 39 and the curved inner surface 41 of tab 40 (see FIG. 5a).

A cannulated bone screw 51 provided with head 52 and longitudinal bore 53 is shown in FIG. 7. The total length of the screw body (excluding the head) is e.g. 90.0 mm., while the length of the threaded portion of the screw is about 20.0 mm. Screw 51 contains a recess in head 52 to receive the driving element of a hexagonal screwdriver.

The instrumentation illustrated in FIGS. 1 to 7 is preferably constructed of stainless steel. The use of this instrumentation in a surgical procedure for the fixation of a fracture in the neck of a right femur, represented by fracture line F, is illustrated in FIGS. 8 to 14. The ultimate goal of this procedure is to place three parallel cannulated bone screws across the fracture line in the triangular peripheral configuration shown in FIG. 14 (a cross-section of the femoral neck), with the threaded portions of the screws located entirely within the femoral head and the heads of the screws tightened against the hard cortical bone of the femoral shank to achieve compression of the bone fragments at the fracture line. Alternatively, four parallel screws may be inserted across the fracture, preferably in a diamond-like peripheral arrangement (as viewed in the plane of FIG. 14).

The fracture is first reduced by known techniques and the patient's leg rotated to bring the plane formed approximately by the femoral head, neck and shank towards the anterior-posterior plane. A first set of X-rays of the fractured bone and a reference marker, e.g. a pin taped to the patient's skin above the fracture, are taken in the anterior-posterior and lateral planes. The surgeon then makes a straight incision about 8 cm. long and separates surrounding tissue so as to expose the trochanteric region of the femur. Then, using the first set of X-rays as a guide, he attempts to drill one of the novel surgical guide pin - external sleeve combinations 31 into place at one of the desired positions, e.g., the position defined by line L in FIG. 8 (anterior-posterior plane) and FIG. 9 (lateral plane), across the fracture line by the customary "free-hand" technique. The external sleeve is held in a surgical drill by means of a Trinkle fitting which interacts with flat 35 and depression 36. As the combination is pressed into the bone, the pin and sleeve are forced into the first relative position (shown in FIG. 5) in which relative rotation between the pin and sleeve is not permitted. Preferably, the surgical drill is provided with a positive stop for the guide pin to limit movement of the pin relative to the sleeve in the distal direction. If the cortical bone of the patient's femoral shank is very hard, the surgeon may first use a standard drill bit to pierce the cortical bone, and then continue with the guide pin - external sleeve combination.

After the first pin-sleeve combination has been inserted, the surgeon takes a second set of X-rays in the anterior-posterior and lateral planes. If he has correctly positioned the combination, or if he has at least placed it parallel to the desired position, he may omit the use of adjustable tool 1 and proceed with the use of template tool 21 (see FIG. 11). Sometimes, however, the first combination 31 will be incorrectly positioned with respect to angulation and possibly also linear displacement. In FIGS. 8 and 9, the first inserted combination 31 is shown to be incorrectly positioned with respect to both linear displacement of the point of entry into the femur ($d_1$ in anterior-posterior plane, $d_2$ in lateral plane) and angulation ($0_1$ in the anterior-posterior plane, $0_2$ in lateral plane). In this case adjustable tool 1 is used to correctly insert a second combination 131 along line L. The distance between the intersections of line L and combination 31 with the femoral cortex is set on tool 1 by rotating arm 4 with respect to arm 2. The angulation of line L with respect to the axis of combination 31 is set by angulating guide tube 6 with respect to arm 4. By temporarily placing two free pin-sleeve combinations within bores 3 and 12 and then superimposing tool 1 over the X-ray pictures in the second set, the surgeon can verify by simple manipulations and visual checks the proper combination of settings of the rotation of arm 4 with respect to arm 2, the angulation of guide tube 6 with respect to arm 4 and the rotation of arm 2 about combination 31 that will yield the desired positioning of combination 131 along line L. Then, with the first two of these settings fixed by activating locking nut 7 and locking screw 9, he slides arm 2 over combination 31 (which passes through bore 3) and rotates arem 2 to the desired position in which it is held in place by means of handle 10. Combination 131 is then passed through guide tube 6 and drilled across the fracture along line L (see FIG. 10). Finally, nut 7 and screw 9 are released, tool 1 is removed, and combination 31 is removed, leaving only combination 131 correctly positioned along line L. The correct position of combination 131 may be verified with X-rays.

The next step in the surgical procedure is the drilling into place of another combination 231 at a desired position parallel to combination 131 (see FIGS. 11 and 12), using hand-held template tool 21, fitted over combination 131, as a guide. Finally, another combination 331 is drilled into place at the remaining desired parallel position, with template tool 21 fitted over either combination 131, combination 231, or both. Template tool 21 is then removed, leaving the situation shown in FIG. 12. The correct position of combinations 231 and 331 may be verified with X-rays.

It is now desired to remove the external sleeves only from combinations 131, 231 and 331, thereby leaving surgical guide pins 132, 232 and 332 (behind pin 232 in FIG. 13) in position. The guide pin and external sleeve in each combination are moved into the second relative position described above. This is accomplished by tapping each guide pin forward (by about 5 mm.) in the bone with a mallet until it distal tip is flush with that of its associated external sleeve. Since relative rotation between pins and sleeves is now permitted (about the center of rotation shown in FIG. 5a) and since the spade-like proximal ends of the guide pins are now securely wedged into and held by the cancellous bone, each sleeve may be easily removed from the bone with a surgical drill or by hand, leaving is associated guide pin in place.

The final steps in the surgical procedure are the screwing of cannulated bone screws 51, 151 and 251 in place over guide pins 132, 232 and 332, respectively, with a cannulated hexagonal screwdriver, followed by the removal of said guide pins, most easily by pulling then by hand, and closing of the wound. As shown in FIG. 13, the threaded portions of the screws lie entirely on one side of the fracture line F, i.e. within the femoral head. As a result, substantial compression of the two bone fragments separated by fracture line F can be achieved by tightening the heads, e.g. 52, of the three screws firmly against the exterior wall of the femur, as shown in FIG. 13. Washers can be inserted under the heads of the cannulated screws if the femoral cortical bone is weak. Screws may be provided in 5.0 mm. gradations of length from about 50.0 mm. to about 130.0 mm. (excluding the head), with the length of the threaded portion remaining fixed at about 20.0 mm. The correct screw length may be determined by reading the penetration of the guide pin into the bone with a depth gauge or with calibrated markings on the guide pin or external sleeve. Replacement of a correctly positioned screw with one of a different length is a simple procedure since the guide pins remain in place until the final verification of proper screw positioning by X-rays has taken place.

Several advantages arise from using the novel guide pin - external sleeve combination of the invention rather than a guide pin by itself. First, the combination is much larger in diameter than the pin and thus can be inserted without a strong tendency to wobble, bend or drift away from a straight course. Second, the structural integrity of the healing bone is not sacrificed since the cannulation in the ultimate prosthesis is only as thick as the guide pin. Finally, a separate step to ream out a bore for the ultimate prosthesis, e.g. a bone screw, with a cannulated reamer is no longer required, although a cannulated tapping step may be desirable in cases of very hard cortical bone.

We claim:

1. In combination
   a surgical guide pin having a distal end, a proximal end and a uniform circular cross-section along the major portion of its length between said two ends, and
   a substantially cylindrical external sleeve having a distal end and a proximal end and receiving the guide pin for sliding fit in a centrally disposed longitudinal bore therein,
   with the guide pin being longer than the external sleeve, the guide pin and the external sleeve being provided at their proximal ends with cooperating cutting surfaces, and the guide pin and the external sleeve being provided at their distal ends with means interacting to (1) prevent relative rotational movement between the guide pin and the external sleeve when they are in a first relative position in which the distal tip of the guide pin extends beyond the distal tip of the external sleeve and the proximal tip of the guide pin extends beyond the proximal tip of the external sleeve, and (2) permit relative rotational movement between the guide pin and the external sleeve when they are in a second relative position in which the guide pin is displaced proximally relative to said first relative position.

2. A combinaion of claim 1 wherein said interacting means comprise a flat on the guide pin extending from the distal tip thereof, a taper on the guide pin extending to the distal tip thereof with decreasing cross-sectional area, and an inwardly/distally extending tab at the distal end of the external sleeve, with the length of said tab being less than that of said flat.

3. A combination of claim 2 wherein said second relative position is one in which the distal tip of the guide pin does not extend beyond the distal tip of the external sleeve.

4. A method of inserting a surgical guide pin into the bone of a patient which comprises the steps of
   (a) inserting into the bone of a patient a combination comprising
   a surgical guide pin having a distal end, a proximal end and a uniform circular cross-section along the major portion of its length between said two ends, and
   a substantially cylindrical external sleeve having a distal end and a proximal end and receiving the guide pin for sliding fit in a centrally disposed longitudinal bore therein,
   with the guide pin being longer than the external sleeve, the guide pin and the external sleeve being provided at their proximal ends with cooperating cutting surfaces, and the guide pin and the external sleeve being provided at their distal ends with means interacting to (1) prevent relative rotational movement between the guide pin and the external sleeve when they are in a first relative position in which the distal tip of the guide pin extends beyond the distal tip of the external sleeve and the proximal tip of the guide pin extends beyond the proximal tip of the external sleeve, and (2) permit relative rotational movement between the guide pin and the external sleeve when they are in a second relative position in which the guide pin is displaced proximally relative to said first relative position,
   and with said guide pin and said external sleeve being in said first relative position while said combination is being inserted into the bone of the patient,
   (b) adjusting said combination so that the guide pin and the external sleeve are placed into said second relative position, and
   (c) removing the external sleeve from the bone of the patient while leaving the guide pin in place therein.

5. A method of inserting a surgical guide pin into the bone of a patient which comprises the steps of
   (a) inserting into the bone of a patient an assembly comprising
   a surgical guide pin having a distal end and a proximal end, and
   a substantially cylindrical external sleeve having a distal end and a proximal end and receiving the guide pin for sliding fit in a longitudinal bore therein,
   with the guide pin and the external sleeve being provided at their proximal ends with cooperating cutting surfaces, and
   (b) removing the external sleeve from the bone of the patient while leaving the guide pin in place therein.

* * * * *